United States Patent
Kozol

(10) Patent No.: US 10,869,802 B2
(45) Date of Patent: *Dec. 22, 2020

(54) INFANT JOINT COMPRESSION DEVICE AND METHOD

(71) Applicant: Barbara H. Kozol, Medford, OR (US)

(72) Inventor: Barbara H. Kozol, Medford, OR (US)

( * ) Notice: Subject to any disclaimer, the term of this patent is extended or adjusted under 35 U.S.C. 154(b) by 465 days.

This patent is subject to a terminal disclaimer.

(21) Appl. No.: 15/454,970

(22) Filed: Mar. 9, 2017

(65) Prior Publication Data

US 2017/0181914 A1  Jun. 29, 2017

Related U.S. Application Data

(63) Continuation of application No. 15/192,898, filed on Jun. 24, 2016, now abandoned, which is a (Continued)

(51) Int. Cl.
*A61H 1/00* (2006.01)
*A61B 5/024* (2006.01)
(Continued)

(52) U.S. Cl.
CPC ......... *A61H 1/006* (2013.01); *A61B 5/02438* (2013.01); *A61B 5/14542* (2013.01); *A61B 5/6802* (2013.01); *A61F 5/03* (2013.01); *A61F 5/3746* (2013.01); *A61B 2503/04* (2013.01); *A61B 2503/045* (2013.01); *A61H 2201/0221* (2013.01); *A61H 2201/165* (2013.01); *A61H 2201/169* (2013.01); *A61H 2201/5082* (2013.01); *A61H 2230/06* (2013.01); *A61H 2230/207* (2013.01)

(58) Field of Classification Search
CPC .......... A61F 5/37; A61F 5/3784; A41B 13/06; A41B 13/08; A41B 13/065; A47D 15/008; A41D 13/1272; A41D 13/1281; A41D 1/002
USPC ........ 128/870–873, 874–876; 2/69.5, 70, 75, 2/80, 83
See application file for complete search history.

(56) References Cited

U.S. PATENT DOCUMENTS

| | | | |
|---|---|---|---|
| 1,332,357 A | | 3/1920 | Parent |
| 2,227,751 A | * | 1/1941 | Idelman ................ A41B 13/06 |
| | | | 2/69.5 |

(Continued)

OTHER PUBLICATIONS

8oz_polyester_fleece.PDF (accessed from www.amazon.com Apr. 2019) (Year: 2019).*

*Primary Examiner* — Rachael E Bredefeld
*Assistant Examiner* — Caitlin A Carreiro
(74) *Attorney, Agent, or Firm* — Schwabe Williamson & Wyatt, PC

(57) ABSTRACT

An infant joint compression device and methods of use including decreasing the length of stay in a neonatal intensive care unit and/or increasing bone density of a premature infant are disclosed. A device can include an elongated, generally cocoon-shaped device pod having a head pod end, a foot pod end and a pod interior extending between the head pod end and the foot pod end; a head opening at the head pod end and communicating with the pod interior; and a pod slit extending from the head opening toward the foot pod end and communicating with the pod interior.

18 Claims, 8 Drawing Sheets

Related U.S. Application Data continuation of application No. 12/813,441, filed on Jun. 10, 2010, now abandoned.

(60) Provisional application No. 61/187,265, filed on Jun. 15, 2009.

(51) Int. Cl.
*A61B 5/145* (2006.01)
*A61B 5/00* (2006.01)
*A61F 5/37* (2006.01)
*A61F 5/03* (2006.01)

(56) References Cited

U.S. PATENT DOCUMENTS

| | | | |
|---|---|---|---|
| 2,521,609 A | 9/1950 | Segerman | |
| 3,739,399 A | 6/1973 | Sheahon | |
| 4,897,885 A * | 2/1990 | Lunt | A41B 13/06 |
| | | | 2/69.5 |
| 4,901,371 A | 2/1990 | Christians | |
| 5,129,406 A | 7/1992 | Magnusen | |
| 5,722,094 A * | 3/1998 | Ruefer | A41B 13/06 |
| | | | 2/69 |
| 6,272,683 B1 * | 8/2001 | Symms | A41B 13/06 |
| | | | 2/69.5 |
| 6,393,612 B1 * | 5/2002 | Thach | A41B 13/065 |
| | | | 2/69.5 |
| 6,687,523 B1 * | 2/2004 | Jayaramen | A41D 13/1281 |
| | | | 600/388 |
| 6,839,924 B2 | 1/2005 | Sims | |
| 6,868,566 B2 | 3/2005 | Gatten | |
| 6,928,674 B2 | 8/2005 | Blackburn | |
| 7,076,819 B2 | 7/2006 | Trani | |
| 7,587,772 B2 | 9/2009 | Ward | |
| 2006/0016005 A1 | 1/2006 | Roda | |
| 2006/0206978 A1 * | 9/2006 | Hilton | A41D 1/215 |
| | | | 2/104 |
| 2009/0064390 A1 * | 3/2009 | Beiring | A41B 13/06 |
| | | | 2/80 |
| 2009/0282599 A1 | 11/2009 | Comerford | |
| 2014/0325735 A1 * | 11/2014 | Howard | A41B 13/005 |
| | | | 2/80 |

* cited by examiner

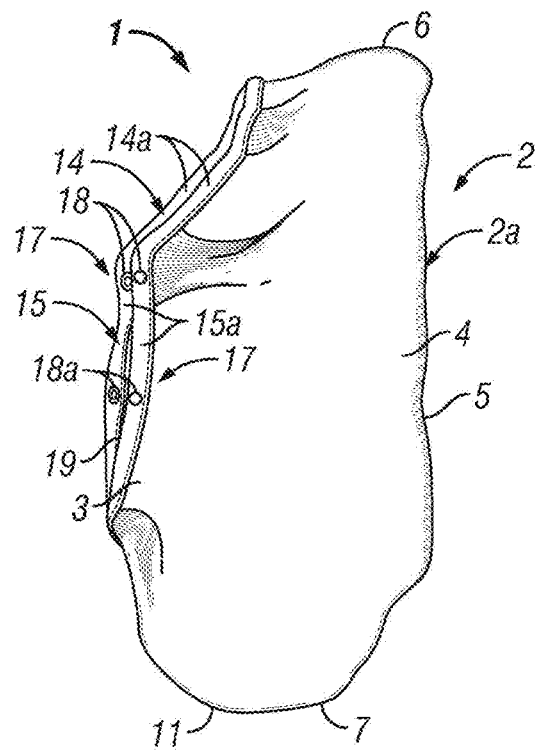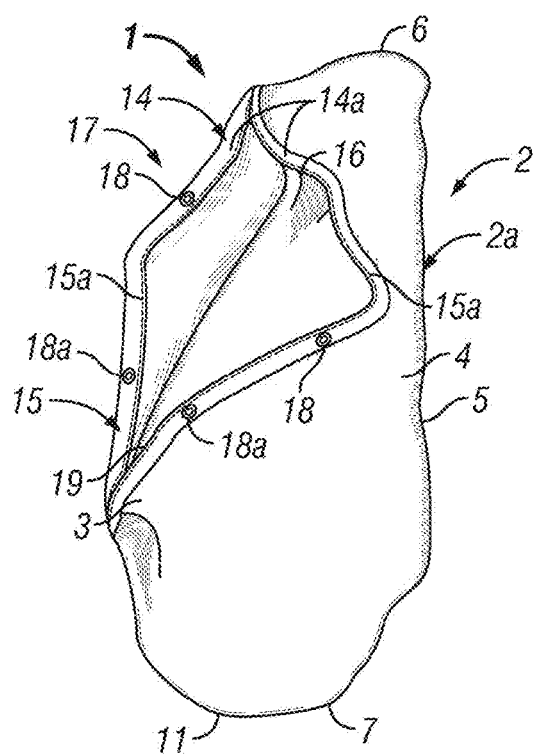
FIG. 1    FIG. 2
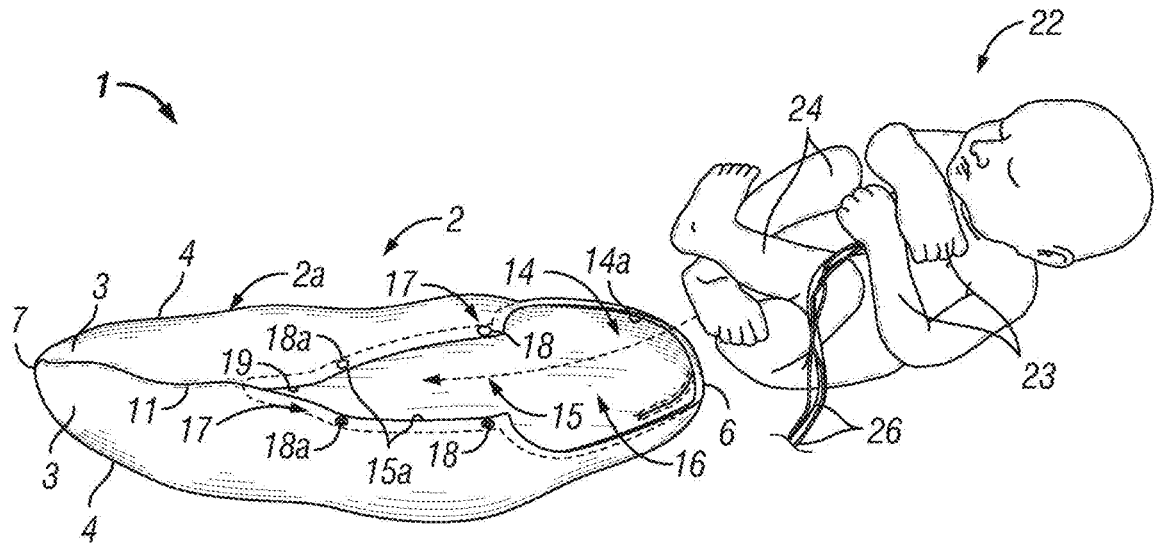
FIG. 3

Table 1. Effect of disclosed device on infant length of stay in NICU.

| Compression Device Subject No. | Gender | GA | d/cGA | LOS |
|---|---|---|---|---|
| 1 | f | 29w4d | 36w1d | 46 |
| 2 | m | 31w2d | 38w1d | 48 |
| 3 | m | 30w4d | 38w0d | 52 |
| 4 | f | 31w3d | 40w0d | 60 |
| 5 | m | 31w5d | 35w5d | 28 |
| 6 | m | 31w5d | 35w6d | 29 |
| 7 | f | 31w4d | 40w6d | 65 |
| 8 | f | 31w4d | 40w6d | 65 |
| 9 | m | 30w0d | 37w0d | 49 |
| 10 | f | 31w6d | 35w6d | 28 |
| 11 | m | 31w6d | 35w6d | 28 |
| 12 | f | 31w4d | 36w0d | 59 |
| 13 | m | 29w6d | 38w5d | 62 |
| 14 | m | 29w4d | 37w6d | 58 |
| 15 | f | 29w3d | 37w4d | 57 |
| 16 | m | 31w3d | 35w4d | 29 |
| 17 | m | 31w3d | 35w3d | 28 |
| 18 | f | 29w6d | 36w6d | 50 |
| 19 | m | 31w5d | 35w4d | 26 |
| 20 | m | 28w4d | 35w3d | 55 |
| 21 | m | 31w4d | 36w3d | 34 |
| 22 | f | 29w2d | 35w2d | 42 |
| *Average* | *13m/9f* | *30w5d* | *37w0d* | *45d* |

FIG. 10

| Control Subject No. | Gender | GA | d/cGA | LOS |
|---|---|---|---|---|
| 1 | m | 31w0d | 37w4d | 46 |
| 2 | f | 31w0d | 37w4d | 46 |
| 3 | f | 31w6d | 36w5d | 34 |
| 4 | m | 28w6d | 36w4d | 54 |
| 5 | m | 28w6d | 35w3d | 46 |
| 6 | m | 32w2d | 36w4d | 36 |
| 7 | f | 28w4d | 36w0d | 52 |
| 8 | f | 28w4d | 36w3d | 55 |
| 9 | m | 30w6d | 35w6d | 35 |
| 10 | f | 30w0d | 36w4d | 46 |
| 11 | f | 30w6d | 36w3d | 39 |
| 12 | m | 28w2d | 38w1d | 69 |
| 13 | f | 29w0d | 37w3d | 59 |
| 14 | m | 30w4d | 38w6d | 58 |
| 15 | m | 28w4d | 37w1d | 60 |
| 16 | m | 28w4d | 39w5d | 78 |
| 17 | m | 28w4d | 39w0d | 73 |
| 18 | m | 30w5d | 39w2d | 60 |
| 19 | m | 30w6d | 35w5d | 34 |
| 20 | f | 29w6d | 37w0d | 49 |
| 21 | f | 31w1d | 40w2d | 64 |
| 22 | m | 29w6d | 38w4d | 52 |
| 23 | f | 28w2d | 38w0d | 68 |
| 24 | f | 31w2d | 40w4d | 65 |
| Average | 13m/11f | 30w0d | 37w4d | 53 d |

FIG. 10 CONT.

Table 2. Effect of disclosed device on infant bone density.

| Device Test No. | Gender | Age | Age at UTS | Initial SOS | Initial density | Exit age | Exit SOS | Exit density | Prog. days | Change in SOS | Change % | Change Z score | LOS |
|---|---|---|---|---|---|---|---|---|---|---|---|---|---|
| 1 | M | 29w4d | 32w4d | 2884 | 21%(-0.8) | 36w3d | 2792 | 4%(-1.8) | 27 | -92 | -17% | -1.0 | 58 |
| 2 | F | 29w3d | 33w2d | 2705 | 1%(-2.4) | 37w1d | 2836 | 4%(-1.8) | 27 | 131 | 3% | 0.6 | 57 |
| 3 | F | 29w6d | 32w2d | 2922 | 34%(-0.4) | 36w1d | 2765 | 2%(-2.0) | 28 | -157 | -32% | -1.6 | 50 |
| 4 | M | 28w4d | 32w1d | 2911 | 30%(-0.5) | 36w1d | 2755 | 2%(-2.1) | 28 | -156 | -28% | -1.6 | 55 |
| 5 | M | 31w4d | 32w5d | 2928 | 33%(-0.5) | 36w3d | 2841 | 5%(-1.7) | 26 | -87 | -25% | -1.2 | 34 |
| 6 | F | 29w2d | 31w4d | 2911 | 33%(-0.4) | 35w2d | 2880 | 12%(-1.2) | 27 | -31 | -21% | -0.08 | 42 |
| Ave. | | 29w4d | | | | | | | | -65.3 | -20% | -0.8 | 49 |

| Control No. | Gender | Age | Age at UTS | Initial SOS | Initial density | Birth age | Exit SOS | Exit density | Prog. days | Change in SOS | Change % | ChangeZ score | LOS |
|---|---|---|---|---|---|---|---|---|---|---|---|---|---|
| 1 | M | 27w4d | 31w3d | 2947 | 46%(-0.1) | 35w2d | 2812 | 8%(-1.4) | 27 | -135 | -38% | -1.3 | 58 |
| 2 | M | 28w4d | 32w5d | 2909 | 27%(-0.6) | 36w5d | 2767 | 2%(-2.1) | 28 | -142 | -25% | -1.5 | 60 |
| 3 | M | 28w4d | 32w5d | 3045 | 70%(0.5) | 36w5d | 2973 | 38%(-0.3) | 28 | -72 | -32% | -0.8 | 78 |
| 4 | M | 28w4d | 32w5d | 3039 | 68%(0.5) | 36w5d | 2971 | 37%(-0.3) | 28 | -68 | -31% | -0.8 | 73 |
| 5 | M | 30w5d | 32w4d | 2890 | 23%(-0.7) | 36w4d | 2875 | 13%(-1.1) | 28 | -15 | -10% | -0.4 | 60 |
| 6 | F | 27w6d | 32w3d | 3040 | 70%(0.5) | 36w3d | 2681 | 0%(-2.8) | 28 | -359 | -70% | -3.3 | 76 |
| 7 | F | 29w6d | 32w2d | 2907 | 29%(-0.6) | 36w1d | 2734 | 1%(-2.2) | 27 | -173 | -28% | -1.6 | 49 |
| 8 | F | 31w1d | 32w5d | 3002 | 57%(0.2) | 35w1d | 2810 | 5%(-1.7) | 28 | -192 | -52% | -1.9 | 64 |
| 9 | M | 29w6d | 31w2d | 2861 | 15%(-1.0) | 35w2d | 2659 | 0%(-3.2) | 28 | -202 | -15% | -2.2 | 52 |
| 10 | F | 28w2d | 32w4d | 2692 | 1%(-2.4) | 36w4d | 2751 | 1%(-2.3) | 28 | 59 | 0% | 0.1 | 68 |
| 11 | F | 31w2d | 32w5d | 2756 | 3%(-1.9) | 36w4d | 2653 | 0%(-2.9) | 27 | -103 | -3% | -1 | 65 |
| Ave. | | | 29w1d | | | | | | | -127 | -28% | -1.34 | 64 |

FIG. 11

INFANT JOINT COMPRESSION DEVICE AND METHOD

CROSS-REFERENCE TO RELATED APPLICATIONS

This application is a continuation-in-part of U.S. patent application Ser. No. 15/192,898 filed Jun. 24, 2016 which is a continuation of U.S. patent application Ser. No. 12/813,441 filed on Jun. 10, 2010 which claims the benefit of U.S. Provisional Application No. 61/187,265, filed Jun. 15, 2009, each of which is hereby incorporated by reference in its entirety.

FIELD OF THE INVENTION

The disclosure generally relates to support systems for premature infants. More particularly, the disclosure relates to a premature infant joint compression device which attempts to mimic the physical conditions provided by the uterus that allow a premature infant/fetus to experience joint compression during spontaneous movement.

BACKGROUND OF THE INVENTION

It is well established in the medical literature that premature infants generally do not grow up to achieve the height of their full-term peers. Premature infants may also be more vulnerable to osteopenia, fractures, etc. than full-term infants. These deficits appear to be caused by the infant's difficulties metabolizing calcium and phosphates. Researchers hypothesize that this is because premature infants lack the experience of pushing against the uterine wall, which in full-term infants causes joint compression that signals the body to synthesize more bone. Extremely low birth weight (ELBW) infants, which are premature infants having birth weights of less than 1500 grams, are the most significantly affected.

Research has demonstrated that when an ELBW infant experiences a joint compression exercise program which is administered by a qualified physical or occupational therapist on a daily basis, that infant develops higher bone density and greater eventual height. The exercise replaces the joint compression experience which the infant would otherwise have had if he or she had continued to full-term in the womb, since the infant would have pushed against the uterine walls. The specially trained therapist holds each of the infant's extremities (arm or leg) supported in an extended position and applies steady pressure on the heel of the hand or foot. This creates proprioceptive feedback (sensory registration of joint pressure) in the wrist, elbow and shoulder of the arm and ankle, knee and hip joints of the leg. Each extremity is held in this extended position in a fluctuating pattern that lasts from several seconds to a few minutes depending on the infant's stability.

Over the past ten years, neonatal intensive care units have emphasized minimal handling of infants and imposition of as little stress as possible to optimize infant rest and brain growth. The 32 week infant grows an average of 150 million brain cells an hour when at optimal rest. Stress not only significantly reduces that number of cells but stress produces cortisol, a substance linked to increased incidence of brain dysfunction. While infants appear to be relaxed during the joint compression exercises after the initial handling and preparation period, it is one more handling event that is not timed or controlled by the infant. Therefore, conventional joint compression exercises can be stressful and tiring to an infant. If performed prior to a feed, joint compression exercises can tire an infant and render his or her feeding efforts less successful. If performed after a feed, the exercises can increase the chances of reflux. At any other time, the exercises can interfere with maximum sleep. Moreover, daily implementation of joint compression exercises by a therapist can become expensive. If a trained therapist is available to provide services in a neonatal intensive care unit (NICU), a typical 30 week premature infant would receive 15 minute treatments 5 days a week for approximately 6 weeks at an average $87 charge for total of $2610.00. The same infant providing his own exercise within a pod device would be charged a maximum of $180 for multiple pods needed for cleanliness purposes and for changing sizes with growth.

Accordingly, there is a need for a premature infant joint compression device and method which effectively and safely provides support for a premature infant to experience joint compression at a time of the infant's choosing. This not only provides the same bone density preservation as more costly and invasive therapy techniques but is less invasive, thereby reducing stress and contributing to optimal brain growth.

SUMMARY

The disclosure is generally directed to an infant joint compression device. An illustrative embodiment of the infant joint compression device includes an elongated, generally cocoon-shaped device pod having a head pod end, a foot pod end and a pod interior extending between the head pod end and the foot pod end; a head opening at the head pod end and communicating with the pod interior; and a pod slit extending from the head opening toward the foot pod end and communicating with the pod interior.

In some embodiments, the infant joint compression device includes an elongated, generally cocoon-shaped device pod having a head pod end, a foot pod end and a substantially unobstructed pod interior extending between the head pod end and the foot pod end; a head opening at the head pod end and communicating with the pod interior; and a pod slit extending from the head opening toward the foot pod end and communicating with the pod interior.

The disclosure is further generally directed to an infant joint compression method. An illustrative embodiment of the method includes providing an infant joint compression device with a device pod having a substantially unobstructed pod interior, placing a premature infant in the pod interior of the device pod and enabling substantially free and unhindered movement of arms and legs of the infant within and outwardly against the device pod.

BRIEF DESCRIPTION OF THE DRAWINGS

The disclosure will now be made, by way of example, with reference to the accompanying drawings, in which:

FIG. 1 is a side view of an illustrative embodiment of the infant joint compression device;

FIG. 2 is a side view of an illustrative embodiment of the infant joint compression device, deployed in a partially-opened position;

FIG. 3 is an exploded perspective view illustrating placement of an infant in an illustrative embodiment of the infant joint compression device;

FIG. 10 is a table (referred to as Table 1) to illustrate the effect of the disclosed device on infant length of stay in NICU; and FIG. 11 is a table (referred to as Table 2) to illustrate the effect of the disclosed device on infant bone density.

DETAILED DESCRIPTION

Figure 3A:
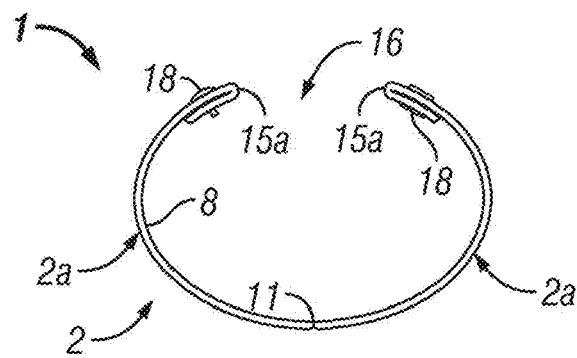
FIG. 3A is a cross-sectional view of an illustrative embodiment of the infant joint compression device.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Referring initially to FIGS. 1-3A of the drawings, an illustrative embodiment of the infant joint compression device, hereinafter device, is generally indicated by reference numeral 1. The device 1 includes a device pod 2 which has a generally elongated, cocoon-shaped configuration with a head pod end 6 and a foot pod end 7 which is opposite the head pod end 6. In some embodiments, the device pod 2 is formed from material such as a fleece material. In some embodiments, the device pod 2 is formed of cotton, knit, rayon, a cotton/knit blend, a cotton/rayon blend or rayon spandex blend. In some embodiments, the device pod 2 may be of polyester fleece, such as an 8-ounce polyester fleece. In some embodiments, the fabric is 4-way stretch to allow unlimited movement of the infant's extremities. Generally, the device pod 2 is constructed from one continuous piece of material making up front, side, and rear of the device to assure minimal seams against the premature infant's delicate skin.

As illustrated in FIG. 3, the device pod 2 has a pod interior 16 with an interior pod surface 8 (FIG. 3A) which faces the pod interior 16. In some embodiments, a head opening 14 is coupled to, for example frames, the pod interior 16 at the head pod end 6. In some embodiments, the head opening 14 has a head opening edge 14a. A generally elongated pod slit 15 extends from the head opening 14 toward the foot pod end 7 and communicates with the pod interior 16. In some embodiments, the pod slit 15 has opposite slit edges 15a which extend from the head opening edge 14a. In some embodiments, fasteners 17 are provided along each of the slit edges 15a. In some embodiments, the fasteners 17 include at least one pair of snaps 18 and 18a, as illustrated. In other embodiments, the fasteners 17 include a zipper, buttons, hook and loop fasteners and/or any other suitable attachment technique which is known by those skilled in the art. In some embodiments, the fasteners 17 include a first pair of snaps 18 adjacent to the head opening 14 and additional snaps 18a spaced-apart from the first pair of snaps 18 toward the foot pod end 7. A wiring passage 19 is defined between the second pair of snaps 18a and the end of the pod slit 15 for purposes which will be hereinafter described. In some embodiments, the device pod 2 is fabricated in one pod section in which case the seam 11 is omitted and the front pod portions 3, the side pod portions 4 and the rear pod portion are fabricated in one piece. As illustrated in FIG. 3A, the entire pod interior 16 is substantially unobstructed from the head pod end 6 to the foot pod end 7 of the device pod 2.

The device pod 2 has various sizes depending on the particular application. In some embodiments, a first size is appropriate for an infant weighing up to 1000 grams (2.2 lbs) a second size appropriate for an infant weighing approximately 1000 to 1500 (2.2 to 3.3 lbs), a third size is for premature infants approximately 1500 to 2000 (3.3 to 4.4 lbs) grams and a fourth largest size is for 2000 to 2500 grams (4.4 to 5.5 lbs).

Figure 4:
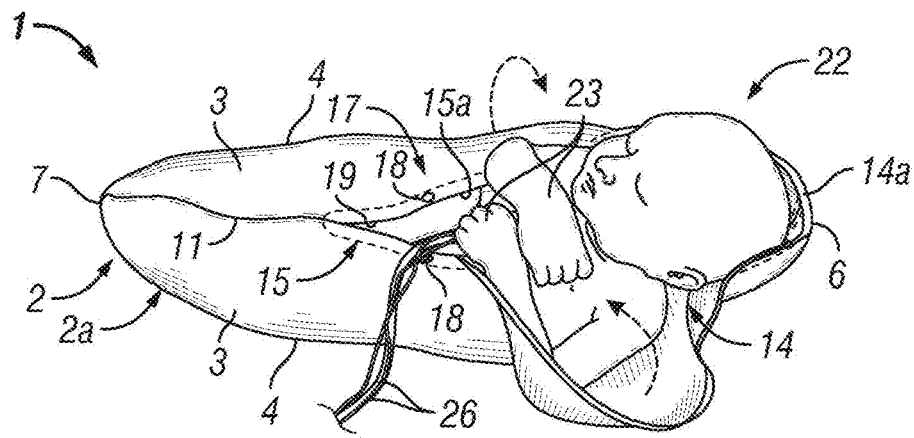
FIG. 4 is a top perspective view of an illustrative embodiment of the infant joint compression device, with the infant partially placed in the device.
Figure 5:
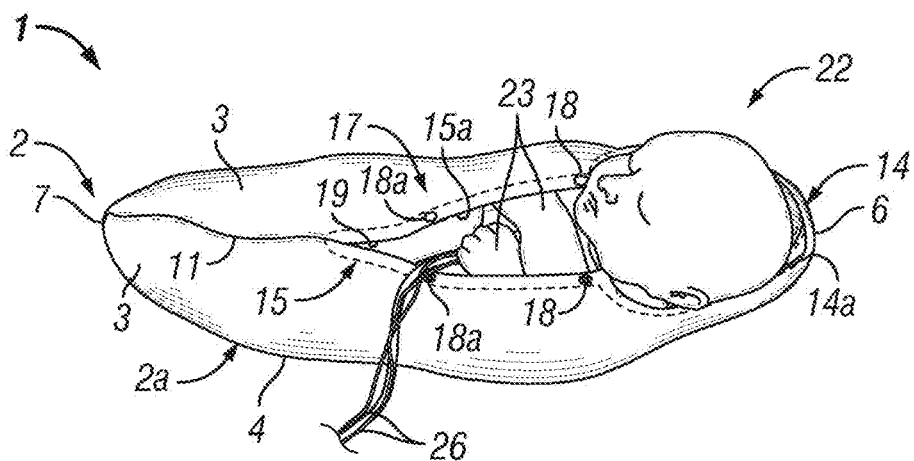
FIG. 5 is a top perspective view of an illustrative embodiment of the infant joint compression device, with the infant fully-placed in the device and the device in an unfastened configuration.
Figure 6:
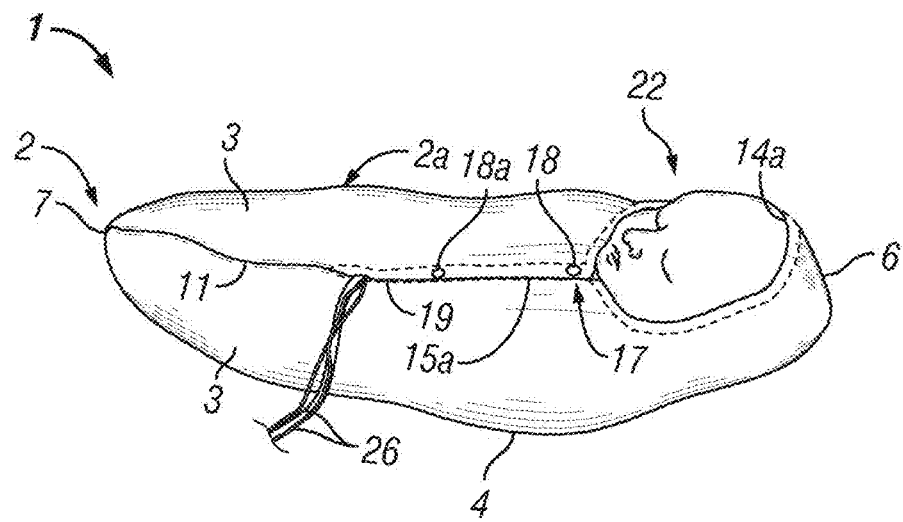
FIG. 6 is a top perspective view of an illustrative embodiment of the infant joint compression device, with the infant fully placed in the device and the device in a fastened configuration.
Figure 7:
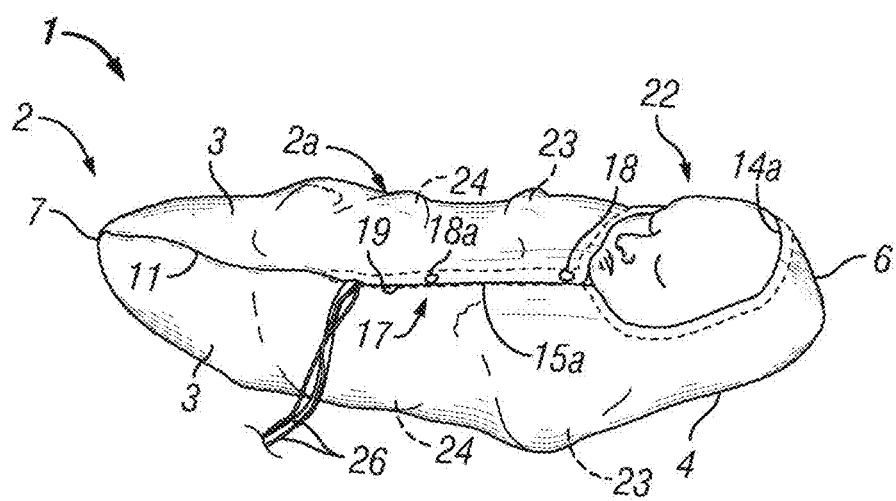
FIG. 7 is a top perspective view of an illustrative embodiment of the infant joint compression device, with the infant fully placed in the device and the device in a fastened configuration, more particularly illustrating free and unhindered movement of the infant's arms and legs (illustrated in phantom) outwardly against the interior surface of the device.

Referring next to FIGS. 3 and 4-7 of the drawings, in exemplary application of the device 1, a premature infant 22 may be placed in the pod interior 16 of the device pod 2. As stated previously the device is designed to be used in a neonatal intensive care unit of a hospital only. Accordingly, in one embodiment, the pod slit 15 is opened and the slit edges 15a separated to facilitate placement of the premature infant 22 in the pod interior 16, as illustrated in FIG. 3. After the premature infant 22 is placed in the pod interior 16, as illustrated in FIGS. 4 and 5, the fasteners 17 are engaged with each other to close the pod slit 15 and secure the slid edges 15a to each other. As illustrated in FIGS. 6 and 7, wiring 26 is connected to instrumentation (not illustrated) that is placed on the premature infant 22 for the purpose of monitoring heart rate, oxygen saturation and other vital signs of the premature infant 22. While this wiring is standard protocol for premature infants it is also necessary for infants utilizing the pod devices to assure they do not compromise their breathing efforts by turning their face into the hood of the pod. The wiring 26 trails from the device pod 2 through the wiring passage 19 in the pod slit 15. As illustrated in FIG. 7, the premature infant 22 is in a naturally flexed position and is capable of stretching and moving his or her arms 23 and legs 24 outwardly against the interior pod surface 8 (FIG. 3A) of the device pod 2 with effort. Since the pod interior 16 can be substantially unobstructed from the head pod end 6 to the foot pod end 7 of the device pod 2, the infant 22 makes these movements in a substantially free and unhindered manner. Accordingly, the stretchable construction of the device pod 2 exerts compression pressure against the bones and joints in the arms 23 and legs 24 of the premature infant 22, facilitating bone growth and development in the same manner as would be the case if the premature infant 22 were inside the womb of the infant's mother. In some embodiments, the premature infant 22 is kept in the device 1 up to 24 hours per day to maximize mild ongoing joint compression. In an exemplary application, the premature infant 22 is kept in the device pod 2 from approximately 28 weeks to approximately 37 weeks of gestation while cared for in a neonatal intensive care unit. The device 1 can be changed from time to time as needed when soiled or otherwise required for hygiene purposes. The premature infant 22 can be continuously monitored particularly during the first two to three hours of use of the device 1 to ensure that the correct temperature is maintained in an effort to avoid chilling or overheating of the premature infant 22. Optionally, blankets (not illustrated) are loosely placed over the premature infant 22 but should not be wrapped tightly around the infant 22 since tight wrapping of the infant 22 may reduce or eliminate the therapeutic effect of the device 1.

Figure 8:
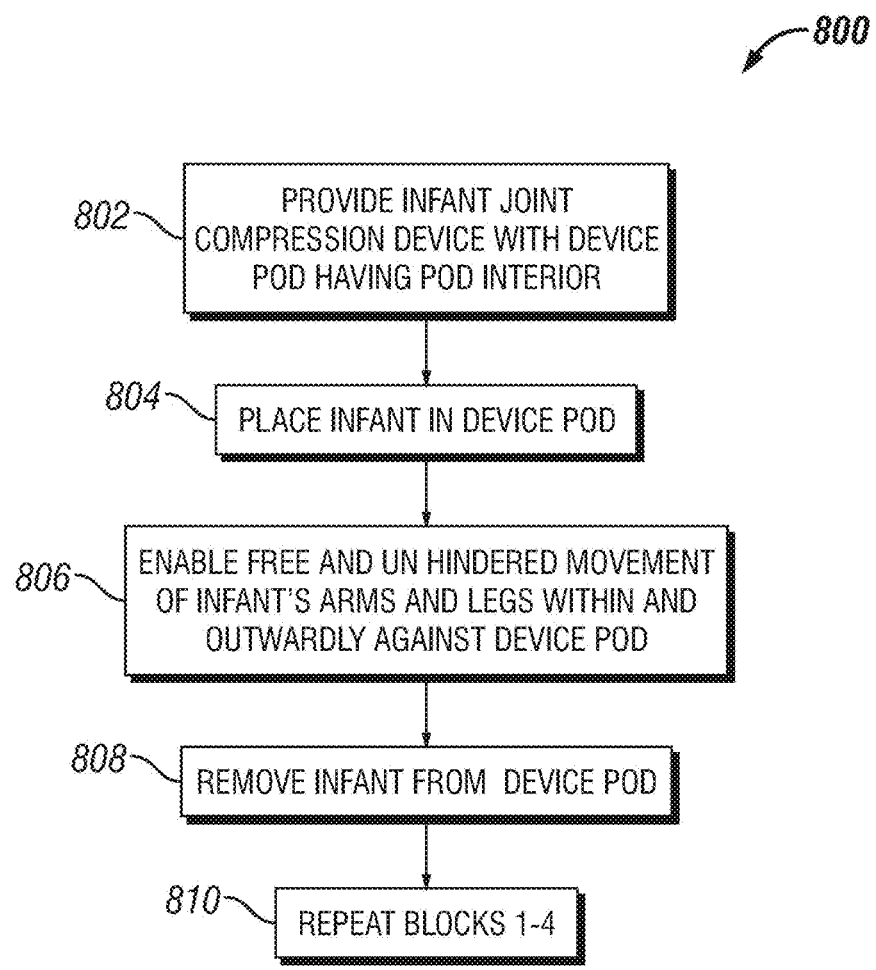
FIG. 8 is a flow diagram of an illustrative embodiment of an infant joint compression method.
Figure 9:
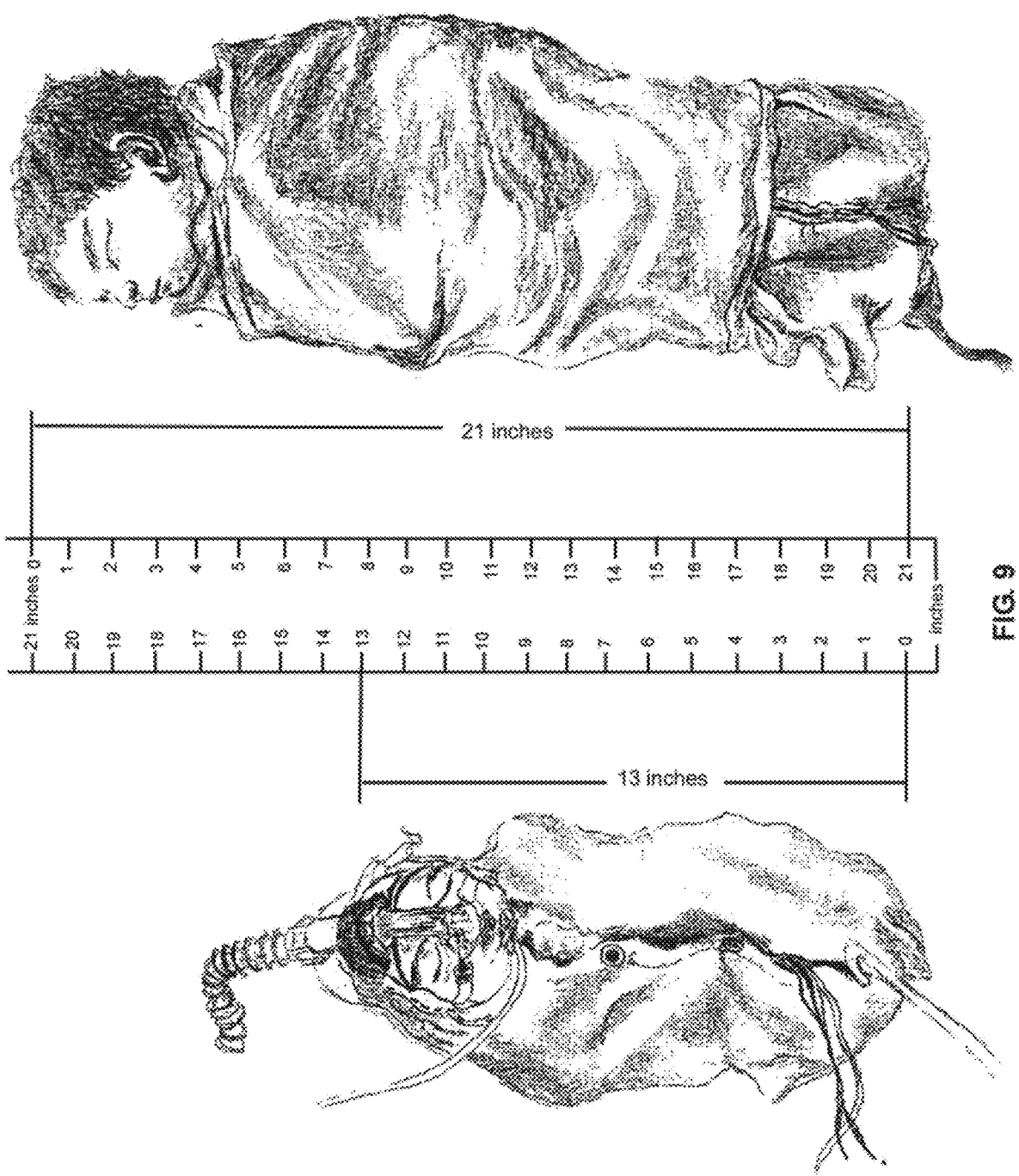
FIG. 9 is a schematic illustrating the differences between a disclosed compression device on a premature infant and a typical swaddling garment on a full term infant.

Referring next to FIG. 8 of the drawings, a flow diagram 800 of an illustrative embodiment of an infant joint compression method is illustrated. In block 802, an infant joint compression device with a device pod having a pod interior is provided. The device pod can have the same design as the device pod 2 which was heretofore described with respect to FIGS. 1-7. In block 804, a premature infant is placed in the device pod. In block 806, free and unhindered movement of the infant's arms and legs within and outwardly against the device pod is enabled. In block 808, the infant may be periodically removed from the device pod for purposes of washing or changing the infant compression device. In block 810, blocks 802-808 are optionally repeated.

In some embodiments, a method of decreasing a premature infant's duration of stay in an intensive care unit is disclosed. For example, the method includes placing a premature infant into a disclosed compression joint device for an extended period of time, usually until the premature infant is discharged from the NICU or until the infant reaches the time period of full gestational term, such as between 4 to 8 weeks, 2 to 4 weeks, 1 to 6 weeks, including 1 week, 2 weeks, 3 weeks, 4 weeks, 5 weeks, 6 weeks, 7 weeks, or 8 weeks. In some embodiments, a method of enhancing one more physical attributes in a premature infant such as bone growth, bone density and/or muscle development, is disclosed. For example, the method includes placing a premature infant into a disclosed compression joint device for an extended period of time to allow bone growth, bone density, and/or muscle strength to be maintained or sustained. It is contemplated that the infant would be removed for brief periods of time to change a soiled device or other procedures.

EXAMPLES

Example 1

This example illustrates the ability of a disclosed infant joint compression device to decrease the length of stay (LOS) of a premature infant in the neonatal intensive care unit. Subjects were all between 28 and 32 weeks gestation at birth and in good health, typical weight, with no medical conditions requiring other than routine care, routine medications, and routine diet. Infants were divided into two groups matching for birth age. At between 28-32 weeks a set of premature infants were placed in an infant joint compression devices comprised of cotton knit usually for infants under about 32 weeks at which time they would typically graduate to 8 oz fleece at approximately 32 weeks gestation, which they remained in continually except for brief periods of 15-30 minutes for four weeks. Another control group received routine neonatal intensive care unit (NICU) care and positioning except they received a ten minute exercise program 5 days a week for four weeks. As demonstrated in Tables 1 and 2 (see FIGS. 10 and 11, respectively), infants that utilized a disclosed joint compression device on average were in the NICU for 45 days. Those which did not receive the treatment spent on average 53 days in the NICU. GA (gestational age); d/cGA (discharge gestational age); LOS (length of stay). Also, the average bone density as measured by ultrasound speed of sound (SOS). SOS showed decreased bone loss compared to the control group (pod −0.85, control 1-1.1250).

Example 2

This example illustrates a study for characterizing a disclosed joint compression device such as the effects on length of stay in the NICU, bone density, bone mass and/or weight. Sixty subjects (30 test infants in a disclosed infant joint compression device, 30 exercise controls) of healthy, premature infants recruited from the NICUs. Infants eligible for the study will be between 28 to 33 weeks gestation with appropriate weight for age. They will be tolerating enteral feeds at >110 kcal/kg of body weight/day on entrance into the study, have no supplemental oxygen requirements, and will be on no medications other than routine vitamins with iron or caffeine.

Infants will be assigned to either a disclosed infant joint compression device or bone stimulation exercise group on entry into the study. Infants will be matched by gestational age at birth, birth weight, and sex. An ultrasound of the left tibia will be obtained. A repeat ultrasound will then be completed, along with age at completion of study between 36 to 37 weeks of age. All infants will be in the study a minimum of 4 weeks. Discharge weight and ultimate length of stay will also be examined.

Infants in the study group will be placed in a properly sized 4-way stretch fleece "pod" with no clothing except a diaper. The pod is designed to provide gentle resistance to any stretching movement, much like that experienced in-utero. The infant will remain in this pod 24 hours a day except when changed, bathed, or being held skin to skin by a parent. Infants will not be swaddled, restricting movement, but may have a blanket loosely laid over them if warmth becomes an issue. Infants needing to be placed in a prone position for short periods will have the pod partially opened to allow for safe positioning. Infants who become ill, develop supplemental oxygen requirements, or require ongoing prone positioning due to gastroesophageal reflux will be discontinued from the study.

Infants in the control group (bone stimulation/joint compression program) will receive standard NICU care and will be provided with approximately 10 minutes a day, 5 days a week of joint compression exercises patterned. At the conclusion of the study primary outcome reviewed will be changes in bone density shown by ultrasound. Comparison of weight gain during the study duration will also be examined, as well as overall length of stay.

It is believed that infants can grow and strengthen their bones through self-regulated exercise within a gently resistive fabric "pod" that simulates the in-utero environment and that self-regulated exercise is at least as effective as that provided by therapists. In addition to the self-regulated exercise being less aversive and stressful to the infant, it is more cost effective than daily interventions by a therapist. A disclosed device will retail at approximately $20.00 whereas a 10 to 15 minute session of therapy currently costs approximately $80.00 per day, usually continuing over several weeks.

While the disclosure has been described in connection with various illustrative embodiments, it is not intended to limit the scope of the appended claims to the particular form set forth, but on the contrary, is intended to cover such alternatives, modifications and equivalents as may be included within the spirit and scope of the disclosure.

What is claimed is:

1. A method for increasing bone density of a premature infant in a neonatal intensive care unit, comprising:
    positioning a premature infant joint compression device around the premature infant so that the premature infant is in a naturally flexed position and is capable of stretching and moving his or her arms and legs outwardly against an interior surface of the premature infant joint compression device with effort, the premature infant joint compression device comprising:
        an elongated, device pod including a stretchable material and having a head pod end, a foot pod end and a pod interior extending between the head pod end and the foot pod end, wherein the pod interior is sized for receiving the premature infant and the head pod end is configured for covering a back of a head and around a neck of the premature infant;
        a head opening at the head pod end configured to extend from an area directly above forehead of the premature infant down each side of a face of the premature infant and covering both ears to terminate at an area directly under a chin of the premature infant and communicating with the pod interior;
        a pod slit extending from the head opening toward the foot pod end and communicating with the pod interior;
        a series of fasteners positioned along an outer edge of the pod slit;
        a wire passage within the series of fasteners positioned along an outer edge of the pod slit for wire passage; and
        wherein the device is positioned only around the premature infant;
    fastening the series of fasteners along the outer edge of the pod slit of the premature infant joint compression device to create compression in the joints of the arms, legs and spine of the premature infant during normal movement patterns of the infant resulting in expansion and contraction of the stretchable material; and
    monitoring one or more vital signs of the premature infant, wherein monitoring one or more vital signs of the premature infant comprises connecting wiring from an instrumentation for vital sign monitoring to the premature infant via passing the wiring through the wire passage within the series of fasteners positioned along the outer edge of the pod slit; and
    increasing bone density of the premature infant as compared to bone density of a premature infant not treated with the premature infant joint compression device, by retaining the premature infant joint compression device around the premature infant to exert compression pressure against the bones and joints in the arms and legs of the premature infant until the infant is discharged or until they reach full gestational term which results in increasing bone density of the premature infant in the neonatal intensive care unit.

2. The method of claim 1, wherein the pod interior is sized for receiving a premature infant weighing up to 1000 grams.

3. The method of claim 1, wherein the pod interior is sized for receiving a premature infant weighing between 1000-1500 grams.

4. The method of claim 1, wherein the pod interior is sized for receiving a premature infant weighing between 1500-2000 grams.

5. The method of claim 1, wherein the pod interior is sized for receiving a premature infant weighing between 2000 to 2500 grams.

6. The method of claim 1, wherein monitoring one or more vital signs of the premature infant comprises monitoring at least heart rate and/or oxygen saturation of the premature infant.

7. The method of claim 1, wherein the method is performed from approximately 28 weeks to approximately 37 weeks of gestation.

8. The method of claim 1, wherein the device pod comprises 8-ounce polyester 4-way stretch fleece.

9. The method of claim 1, wherein the device pod is formed of a single piece of material with two seams.

10. A method for decreasing a length of stay of a premature infant in a neonatal intensive care unit, comprising:
    positioning a premature infant joint compression device around the premature infant so that the premature infant is in a naturally flexed position and is capable of stretching and moving his or her arms and legs outwardly against an interior surface of the premature infant joint compression device with effort, the premature infant joint compression device comprising:
        an elongated, device pod including a stretchable material and having a head pod end, a foot pod end and a pod interior extending between the head pod end and the foot pod end, wherein the pod interior is sized for receiving the premature infant and the head pod end is configured for covering a back of a head and around a neck of the premature infant;
        a head opening at the head pod end configured to extend from an area directly above a forehead of the premature infant down each side of a face of the premature infant and covering both ears to terminate at an area directly under a chin of the premature infant and communicating with the pod interior;
        a pod slit extending from the head opening toward the foot pod end and communicating with the pod interior;
        a series of fasteners positioned along an outer edge of the pod slit;
        a wire passage within the series of fasteners positioned along an outer edge of the pod slit for wire passage; and
        wherein the device is positioned only around the premature infant;
    fastening the series of fasteners along the outer edge of the pod slit of the premature infant joint compression device to create compression in the joints of the arms, legs and spine of the premature infant during normal movement patterns of the premature infant resulting in expansion and contraction of the stretchable material;
    monitoring one or more vital signs of the premature infant, wherein monitoring one or more vital signs of the premature infant comprises connecting wiring from an instrumentation for vital sign monitoring to the infant via passing the wiring through the wire passage within the series of fasteners positioned along the outer edge of the pod slit; and retaining the premature infant joint compression device around the premature infant for substantially 2 to 6 weeks which decreases the length of stay of the premature infant in the neonatal intensive care unit.

11. The method of claim 10, wherein the pod interior is sized for receiving a premature infant weighing up to 1000 grams.

12. The method of claim 10, wherein the pod interior is sized for receiving a premature infant weighing between 1000-1500 grams.

13. The method of claim 10, wherein the pod interior is sized for receiving a premature infant weighing between 1500-2000 grams.

14. The method of claim 10, wherein the pod interior is sized for receiving a premature infant weighing between 2000 to 2500 grams.

15. The method of claim 10, wherein monitoring includes monitoring at least heart rate and/or oxygen saturation of the premature infant.

16. The method of claim 10, wherein the method is performed from approximately 28 weeks to approximately 37 weeks of gestation.

17. The method of claim 10, wherein the device pod comprises 8-ounce polyester 4-way stretch fleece.

18. The method of claim 10, wherein the device pod is formed of a single piece of material with two seams.

* * * * *